(12) United States Patent
Barry et al.

(10) Patent No.: US 7,037,666 B2
(45) Date of Patent: May 2, 2006

(54) METHODS FOR IDENTIFYING MODULATORS OF THE INTERACTION BETWEEN LAP (LATENCY ASSOCIATED PEPTIDE) AND INTERGRIN $\alpha_v\beta_3$ AND MEDICAL USE THEREOF

(75) Inventors: Simon Barry, Macclesfield (GB); Carmel Horgan, Stevenage (GB); Steven Ludbrook, Stevenage (GB); David Miller, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/276,947

(22) PCT Filed: May 25, 2001

(86) PCT No.: PCT/GB01/02352

§ 371 (c)(1),
(2), (4) Date: May 5, 2003

(87) PCT Pub. No.: WO01/90186

PCT Pub. Date: Nov. 29, 2001

(65) Prior Publication Data

US 2003/0176315 A1 Sep. 18, 2003

(30) Foreign Application Priority Data

May 26, 2000 (GB) .................................. 0012991.6
Jan. 5, 2001 (GB) .................................. 0100286.4

(51) Int. Cl.
*G01N 33/53* (2006.01)
(52) U.S. Cl. ........................................ 435/7.1; 435/7.21
(58) Field of Classification Search ................. 435/7.1, 435/7.21
See application file for complete search history.

(56) References Cited

U.S. PATENT DOCUMENTS

| 5,780,426 A | 7/1998 | Palladino et al. |
| 6,037,176 A | 3/2000 | Bennett et al. |

FOREIGN PATENT DOCUMENTS

| WO | WO 96/00730 | 1/1996 |
| WO | WO 97/451371 | 12/1997 |
| WO | WO 98/46265 | 10/1998 |

OTHER PUBLICATIONS

Ludbrook et al. The integrin alphavbeta3 is a receptor for the latency-associated peptides of transforming growth factors beta1 and beta3. Biochem J. Jan. 15, 2003;369(Pt 2):311-8.*

Kuntz. Structure-based strategies for drug design and discovery. Science. 1992 257(5073):1078-1082.*

Miller et al Ligand binding to proteins: the binding landscape model. Protein Sci. Oct. 1997;6(10):2166-79.*

Brooks et al., "Integrin alphavbeta3 antagonists promote tumor regression by inducing apoptosis of angiogenic blood vessels," *Cell* 79(7):1157-1164 (Dec. 1994).

Carron et al., "A peptidomimetic antagonist of the integrin alpha v beta 3 inhibitsleydig cell tumor growth and the development of hypercalcemia of malignancy," *Cancer Research* 58:1930-1935 (May 1998).

Hammes et al., "Subcutaneous injection of a cyclic petide antagonist of vitronectin receptor-type integrins inhibits retinal neovascularization," *Nature Medicine* 2(5):529-533 (May 1996).

Horton, "The alphavbeta3 integrin vitronectin receptor," *International Journal of Biochemistry and Cell Biology* 29(5):721-725 (May 1997).

Munger et al., "Interactions between growth factors and integrins: Latent forms of transforming growth factor-beta are ligands for the integrin alphavbeta1," *Molecular Biology of the Cell* 9(9):2627-2638 (1998).

Munger et al., "The integrin alphavbeta6 binds and activates latent tgfbeta1: A mechanism for regulating pulmonary inflammation and fibrosis," *Cell* 96:319-328 (Feb. 1999).

Sulyok et al., "Solid-phase synthesis of a nonpeptide RGD mimetic library: New selective alphavbeta3 integrin antagonists," *Journal of Medicinal Chemistry* 44(12):1938-1950 (Jun. 2001).

Blystone et al., "Integrin beta3 cytoplasmic tail is necessary and sufficient for regulation of alpha5beta1 phagocytosis by alphavbeta3 and integrin-associated protein," *Journal of Cell Biology* 130(3):745-754 (Aug. 1995).

Keenan et al., "Discovery of potent nonpeptide vitronectin receptor (alphavbeta3) antagonists," *Journal of Medicinal Chemistry* 40(15):2289-2292 (Jul. 1997).

* cited by examiner

*Primary Examiner*—Christina Chan
*Assistant Examiner*—Maher Haddad
(74) *Attorney, Agent, or Firm*—Virginia G. Campen

(57) ABSTRACT

A method for the identification of a modulator of the interaction between latency asssociated peptide (LAP) of transforming growth factor β1 (TGF-β1) and the integrin $a_vb_3$, which method comprises: (a) providing, as a first component, LAP-β1 or a functional variant thereof (b) providing, as a second component, integrin $a_vb_3$ or a functional variant thereof (c) contacting the two components with a test product under conditions that, in the absence of the test product, would permit the two components to interact; and (d) determining whether the test product is capable of modulating the interaction between the first and second components, thereby to determine whether the test product is a modulator of the interaction between LAP-β1 and integrin $a_vb_3$.

6 Claims, 6 Drawing Sheets

SEQUENCE LISTING

<160> NUMBER OF SEQ ID NOS: 1

<210> SEQ ID NO 1
<211> LENGTH: 390
<212> TYPE: PRT
<213> ORGANISM: Homo sapiens

<400> SEQUENCE: 1

```
Met Pro Pro Ser Gly Leu Arg Leu Leu Leu Leu Leu Pro Leu Leu
 1               5                  10                  15

Trp Leu Leu Val Leu Thr Pro Gly Arg Pro Ala Ala Gly Leu Ser Thr
                 20                  25                  30

Cys Lys Thr Ile Asp Met Glu Leu Val Lys Arg Lys Arg Ile Glu Ala
             35                  40                  45

Ile Arg Gly Gln Ile Leu Ser Lys Leu Arg Leu Ala Ser Pro Pro Ser
         50                  55                  60

Gln Gly Glu Val Pro Pro Gly Pro Leu Pro Glu Ala Val Leu Ala Leu
 65                  70                  75                  80

Tyr Asn Ser Thr Arg Asp Arg Val Ala Gly Glu Ser Ala Glu Pro Glu
                 85                  90                  95

Pro Glu Pro Glu Ala Asp Tyr Tyr Ala Lys Glu Val Thr Arg Val Leu
                100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
                180                 185                 190

Pro Glu Trp Leu Ser Phe Asp Val Thr Gly Val Val Arg Gln Trp Leu
            195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240
```

-continued

```
Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
    370                 375                 380

Arg Ser Cys Lys Cys Ser
385                 390
```

METHODS FOR IDENTIFYING MODULATORS OF THE INTERACTION BETWEEN LAP (LATENCY ASSOCIATED PEPTIDE) AND INTERGRIN $\alpha_V\beta_3$ AND MEDICAL USE THEREOF This application is filed pursuant to 35 U.S.C. § 371 as a United States National Phase Application of International Application No. PCT/GB01/02352 filed May 25, 2001, which claims priority from Great Britain Application No. 0012991.6 filed in the United Kingdom on May 26, 2000 and Great Britain Application No. 0100286.4 filed in the United Kingdom on Jan. 5, 2001.

FIELD OF THE INVENTION

The invention relates to medical products for use in immunomodulation and use in the treatment of inflammatory and fibrotic diseases and cancer, diabetic retinopathy, bone resorption and osteoporosis. The invention also relates to methods for identifying products which are useful in therapy, particularly in immunomodulation and in the treatment of inflammatory and fibrotic diseases and fibrotic diseases and cancer, diabetic retinopathy, bone resorption and osteoporosis.

BACKGROUND TO THE INVENTION

The integrins comprise a large family of heterodimeric transmembrane receptors that mediate both cell-cell and cell-matrix interactions. They engage numerous ligands and regulate a variety of cellular and physiological processes such as cell proliferation, apoptosis, migration, differentiation, inflammation, and tissue remodelling. The $\alpha_v\beta_3$ integrin has a widespread distribution including endothelial cells, smooth muscle cells, a variety of monocyte-derived cells, tumor cells, platelets, mesenchymal fibroblasts, T lymphocytes, and dentritic cells. It has received particular attention because of the role it plays in tumor angiogenesis.

The transforming growth factor-β (TGF-β) isoforms TGF-β1, TGF-β2 and TGF-β3 are expressed from numerous cell types and are present in virtually all tissues. They potently inhibit cellular proliferation of many cell types, and also induce extracellular matrix synthesis, integrin expression, and modulate immune responses. They are synthesised as large precursor proteins that are proteolytically processed in the golgi to yield a mature TGF-β protein of approximately 110 amino acids and an amino terminal protein called latency associated protein-β (LAP-β) of approximately 280 amino acids. These two proteins homodimerise and the two dimers also interact to form a LAP-β-TGF-β complex containing two parts of each protein. This complex renders TGF-β inactive, and activation requires some conformational change and/or proteolysis of the LAP-β protein.

SUMMARY OF THE INVENTION

This invention is based on our finding that the integrin, $\alpha_v\beta_3$, binds the latency associated peptide-β1 (LAP-β1) of transforming growth factor-β1 (TGF-β1). The interaction between $\alpha_v\beta_3$ and LAP-β1 of TGF-β2 provides a link between that interaction and a number of biologically significant processes.

According to the present invention there is thus provided a method for the identification of a modulator of the interaction between latency associated peptide-β1 and the integrin $\alpha_v\beta_3$ which method comprises:

(a) providing, as a first component, latency-associated peptide-β1 (LAP-β1) or a functional variant thereof;
(b) providing, as a second component, integrin $\alpha_v\beta_3$ or a functional variant thereof;
(c) contacting the two components with a test product under conditions that, in the absence of the test product, would permit the two components to interact; and
(d) determining whether the test product is capable of modulating the interaction between the first and second components, thereby to determine whether the test product is a modulator of the interaction between LAP-β1 and integrin $\alpha_v\beta_3$.

The method of the invention may also be used to identify modulators of TGF-β1 activity.

The invention also provides:

a test kit for the identification of a modulator of the interaction between LAP-β1 and the integrin $\alpha_v\beta_3$, which kit comprises:
  (i) a first component which is latency-associated peptide-β1 (LAP-β1) or a functional variant thereof; and
  (ii) a second component which is, integrin $\alpha_v\beta_3$ or a functional variant thereof;

a modulator of the interaction between LAP-β1 and integrin $\alpha_v\beta_3$ for use in a method of treatment of the human or animal body;

use of a modulator which is an inhibitor of the interaction between LAP-β1 and integrin $\alpha_v\beta_3$ in the manufacture of a medicament for use in a method of immuno-modulation or in a method of treatment of an inflammatory disease, a fibrotic disease, cancer, diabetic retinopathy, bone resorption or osteoporosis;

use of a modulator which is an activator of the interaction between LAP-β1 and integrin $\alpha_v\beta_3$ in the manufacture of a medicament for use in a method of preventing apoptosis;

a pharmaceutical composition comprising a pharmaceutically acceptable carrier or diluent and, as active ingredient, a product which is a modulator of the interaction between LAP-β1 and integrin $\alpha_v\beta_3$;

a method for treating a host requiring immuno-modulation or suffering from an inflammatory disease, a fibrotic disease, cancer, diabetic retinopathy, bone resorption or osteoporosis which method comprises administering to the host an effective amount of a product which is an inhibitor of the interaction between LAP-β1 and integrin $\alpha_v\beta_3$;

a method for treating a host requiring prevention of apoptosis which method comprises administering to the host an effective amount of an activator of the interaction between LAP-β1 and integrin $\alpha_v\beta_3$;

a modulator of the interaction between LAP-β1 and integrin $\alpha_v\beta_3$ identified by a method of the invention or a test kit of the invention;

a modulator of the interaction between LAP-β1 and integrin $\alpha_v\beta_3$ identified by a method of the invention or a test kit of the invention for use in a method of treatment of the human or animal body by therapy;

use of a modulator of the interaction between LAP-β1 and integrin $\alpha_v\beta_3$ identified by a method of the invention or a test kit of the invention in the manufacture of a medicament for use in a method of immuno-modulation or a method of treatment of an inflammatory disease, a fibrotic disease, cancer, diabetic retinopathy, bone resorption or osteoporosis;

use of a modulator of the interaction between LAP-β1 and integrin $\alpha_v\beta_3$ identified by a method of the invention or a test kit of the invention in the manufacture of a medicament for use in a method of preventing apoptosis;

a pharmaceutical composition comprising a pharmaceutically acceptable carrier or diluent and, as active ingredient, a modulator of the interaction between LAP-β1 and integrin $\alpha_v\beta_3$ identified by a method of the invention or a test kit of the invention;

a method for treating a host requiring immuno-modulation or suffering from an inflammatory disease, a fibrotic disease, cancer, diabetic retinopathy, bone resorption or osteoporosis, which method comprises administering to the host an effective amount of a modulator of the interaction between LAP-β1 and integrin $\alpha_v\beta_3$ identified by a method of the invention or a test kit of the invention;

a method for treating a host requiring prevention of apoptosis, which method comprises administering to the host an effective amount of a modulator of the interaction between LAP-β1 and integrin $\alpha_v\beta_3$ identified by a method of the invention or a test kit of the invention;

a method for identifying a product which can be used in a method of immuno-modulation or in a method of treatment of an inflammatory disease, a fibrotic disease, cancer, diabetic retinopathy, bone resorption or osteoporosis, which method comprises:
(a) providing, as a first component, latency-associated peptide-β1 (LAP-β1) or a functional variant thereof;
(b) providing, as a second component, integrin $\alpha_v\beta_3$ or a functional variant thereof;
(c) contacting the two components with a test product under conditions that, in the absence of the test product, would permit the two components to interact;
(d) determining whether the test product is capable of inhibiting the interaction between the first and second components; and
(e) determining whether a product identified in step (d) can be used in a method of immuno-modulation or in the treatment of an inflammatory disease, a fibrotic disease, cancer, diabetic retinopathy, bone resorption or osteoporosis;

a method for identifying a product which can be used in a method of preventing apoptosis, which method comprises:
(a) providing, as a first component, latency-associated peptide-β1 (LAP-β1) or a functional variant thereof;
(b) providing, as a second component, integrin $\alpha_v\beta_3$ or a functional variant thereof;
(c) contacting the two components with a test product under conditions that, in the absence of the test product, would permit the two components to interact;
(d) determining whether the test product is capable of activating the interaction between the first and second components; and
(e) determining whether a product identified in step (d) can be used in a method of preventing apoptosis;

a method for treating a host requiring immuno-modulation or suffering from an inflammatory disease, a fibrotic disease, cancer, diabetic retinopathy, bone resorption or osteoporosis, which method comprises:
(a) identifying a product by use of a method for identifying a product which can be used in a method of immuno-modulation or in a method of treatment of an inflammatory disease, a fibrotic disease, cancer, diabetic retinopathy, bone resorption or osteoporosis, which method comprises; and
(b) administering to the host an effective amount of the product; and a method for treating a host requiring prevention of apoptosis, which method comprises:
(a) identifying a product by use of a method for identifying a product which can be used in a method of preventing apoptosis; and
(b) administering to the host an effective amount of the product.

K562-$\alpha_v\beta_3$ cells were allowed to attach to wells coated with a range of concentrations of either LAPβ$_1$ (filled circles), or GST-LAPβ$_1$ amino acids 242–252 (open circles) in the presence of 2 mM MgCl$_2$. The X-axis is expressed as [Integrin binding sites] to account for differences in coated protein size. Each data point represents the mean±SD of duplicate points, and is representative of at least three identical experiments.

Figure 6:
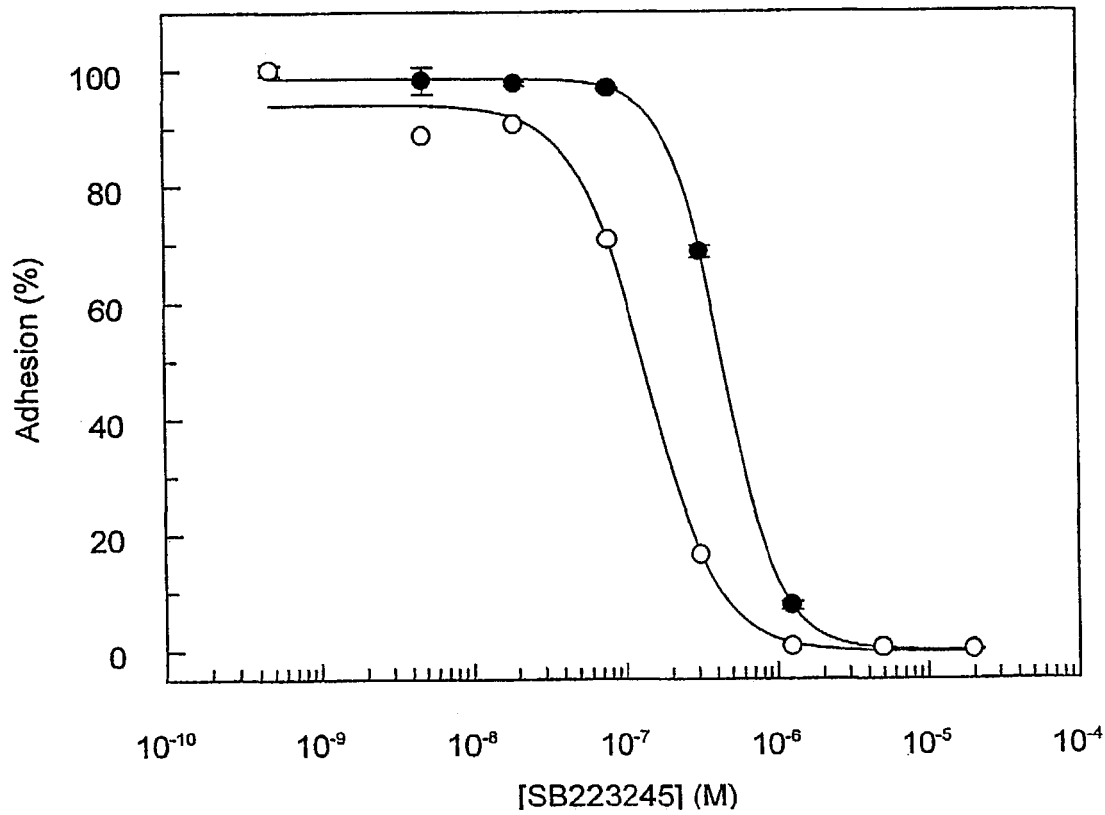

FIG. 6. Inhibition of K562-$\alpha_v\beta_3$ Adhesion to Initact LAPβ$_1$ and GST-LAPβ$_1$ (amino acids 242–252) by SB223245

K562-α$_v$β$_3$ cells were allowed to attach to wells coated with 0.5 µg/well LAPβ$_1$ (open circles) or 0.4 µg/well GST-LAPβ$_1$ amino acids 242–252 (filled circles) in the presence of 2 mM MgCl$_2$. A dose response relationship with SB223245 was performed. Calculated IC$_{50}$ values were LAPPβ$_1$, (442 nM), GST-LAPβ$_1$ (amino acids 242–252 (139 nM). Each data point represents the mean±SD of duplicate points, and is representative of at least three identical experiments.

Figure 7:
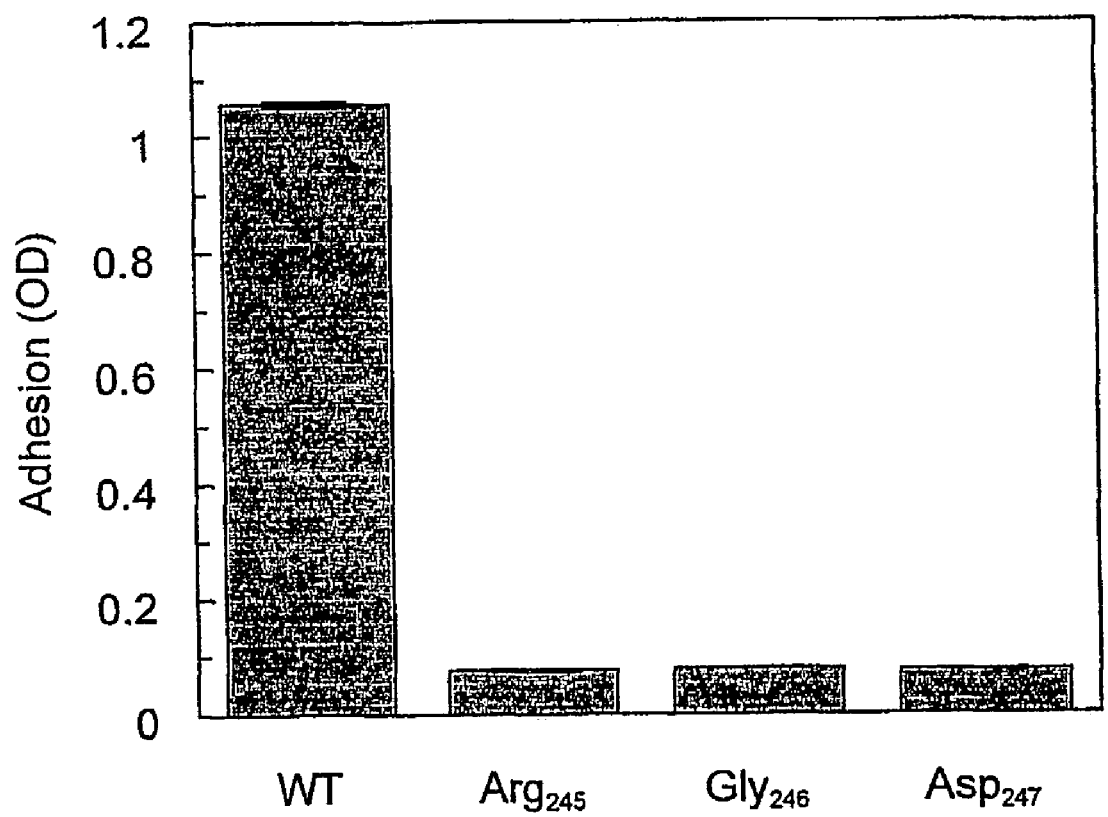

FIG. 7. Critical importance of the LAPβ$_1$ RGD sequence for K562-α$_v$β$_3$ binding.

K562-α$_v$β$_3$ cells were allowed to attach in the presence of 2 mM MgCl$_2$ to wells coated with 0.5 µg of either GST-LAPβ$_1$ amino acids 242–252 (WT), or site specific mutants where either Arg$_{245}$, Gly$_{246}$, or Asp$_{247}$ were mutated to alanine as described under the bars. Each data point represents the mean±SD of duplicate points, and is representative of at least three identical experiments.

DESCRIPTION OF THE SEQUENCE LISTING

SEQ ID NO: 1 (SwissProt Accession No. P01137) sets out the amino acid sequence of human TGF-β1. Amino acids 1 to 29 is the signal sequence; amino acids 30 to 278 is the LAP-β1 sequence; and amino acids 279 to 390 is the mature TGF-β1 cytokine sequence.

DETAILED DESCRIPTION OF THE INVENTION

We have shown, surprisingly, that the integrin, α$_v$β$_3$ binds to the latency associated peptide (LAP-β1) region of transforming growth factor-β1 (TGF-β1). This links the interaction of those two polypeptides with the following biological processes:
 (a) activation of TGF-β1 and subsequent immunomodulation and/or fibrosis mediated by active TGF-β1;
 (b) migration of α$_v$β$_3$-expressing cells along LAP-TGFβ1 protein; and
 (c) protection of α$_v$β$_3$-expressing cells from apoptosis.

Due to the presence of α$_v$β$_3$ on a wide variety of cell types, and the presence of TGF-β1 in many tissues, originating from many cell types, there may be multiple effects of the interaction of α$_v$β$_3$ with LAP-β1 of TGF-β1. Therefore, all cell types that express α$_v$β$_3$ have the potential to interact with LAP-β1. This may modulate cell activation/differentiation via the binding event to α$_v$β$_3$ (i.e. signalling through α$_v$β$_3$) or via the activation of TGFβ1 (i.e. TGF-β1 signalling through TGFβ receptors), and the immunomodulatory (including Th1/Th2 cell switching)/fibrotic effects of activated TGF-β1.

The invention provides methods for identifying a modulator of the interaction between α$_v$β$_3$ and LAP-β1. A suitable method of the invention comprises: providing, as a first component, LAP-β1 or a functional variant thereof; providing, as a second component, integrin α$_v$β$_3$ or a functional variant thereof; contacting the two components with a test product under conditions that, in the absence of the test product, would permit the two components to interact; and determining whether the test product is capable of inhibiting the interaction between the first and second components. The skilled person can thereby readily determine whether the test product is a modulator of the interaction between LAP-β1 and integrin α$_v$β$_3$.

In vivo, TGF-β1 is secreted as a complex composed of three proteins derived from two genes. The TGF-β1 gene encodes a procytokine consisting of a C-terminal TGF-β1 sequence and a larger N-terminal region that after processing forms the latency-associated peptide-β1 (LAP-β1). Both the mature TGF-β1 and LAP-β1 peptides form homodimers and the two homodimers form a noncovalent complex called the small latent complex (SLC). LAP-β1 can disulfide bond to another protein, the latent TGF-β1-binding protein (LTBP); the latent form of TGF-β1 thus formed is called the large latent complex (LLC).

LAP-β1 or a functional variant thereof is provided as a first component. The amino acid sequence of LAP-β1 is set out as amino acids 30 to 278 of SEQ ID NO:1. The sequence of SEQ ID NO: 1 corresponds to that of SwissProt database accession number P01137. LAP-β1 may be used as a monomer, but is more typically used as a homodimer. If a homodimer is used one or both peptides comprising the dimer may be a functional variant of LAP-β1. If both peptides are functional variants they may be different functional variants of LAP-β1.

A functional variant of LAP-β1 is a polypeptide which has a sequence similar to that of amino acids 30 to 278 of SEQ ID NO: 1 and which retains α$_v$β$_3$ binding activity. Typically, the binding activity to α$_v$β$_3$ of a functional variant may be substantially the same as that of LAP-β1. Alternatively, the binding activity of a functional variant may be greater or less than that of LAP-β1. For example, a functional variant may have at least 90% activity, at least 80% activity or at least 70% activity of the LAP-β1 having the sequence set out as amino acids 30 to 278 of SEQ ID NO: 1 with respect to its ability to bind α$_v$β$_3$ A functional variant typically comprises a sequence substantially similar to that set out as amino acids 30 to 278 of SEQ ID NO: 1. Thus a functional variant will generally have at least 60%, at least 70%, at least 80%, at least 90%, at least 95%, at least 98 or at least 99% sequence identity to the LAP-β1 having the sequence set out as amino acids 30 to 278 of SEQ ID NO: 1, calculated over the full length of those sequences. The UWGCG Package provides the BESTFIT program which can be used to calculate identity (for example used on its default settings) (Devereux et al (1984) *Nucleic Acids Research* 12, p387–395). The PILEUP and BLAST algorithms can be used to calculate identity or line up sequences (typically on their default settings), for example as described in Altschul S. F. (1993) J Mol Evol 36:290–300; Altschul, S, F et al (1990) J Mol Biol 215: 403–10. Software for performing BLAST analyses is publicly available through the National Centre for Biotechnology Information (http://www.ncbi.nlm.nih.gov/).

A functional variant may be a naturally occurring sequence, such as a related gene, for example LAP-β3, or an allelic variant of LAP-β1. An allelic variant will generally be of human or non-human mammal, for example bovine or porcine, origin.

Alternatively, a functional variant may be a non-naturally occurring sequence. A non-naturally occurring functional variant may be a modified version of the LAP-β1 having the sequence set out as amino acids 30 to 278 of SEQ ID NO: 1, obtained by, for example, amino acid substitution, deletion or addition. Up to 1, up to 5, up to 10, up to 50 or up to 100 amino acid substitutions or deletions, for example, may be made. Thus, a functional variant of the sequence given as amino acids 30 to 278 of SEQ ID NO: 1 may be a fragment of that sequence. Typically, if substitutions are made, the substitutions will be conservative substitutions, for example according to the following Table. Amino acids in the same block in the second column and preferably in the same line in the third column may be substituted for each other. Deletions are preferably deletions of amino acids from one or both ends of the sequence given as amino acids 30 to 278 of SEQ ID NO: 1. Alternatively, deletions are of regions not involved in the binding of $\alpha_v\beta_3$.

| ALIPHATIC | Non-polar | GAP |
| --- | --- | --- |
| | | ILV |
| | Polar-uncharged | CSTM |
| | | NQ |
| | Polar-charged | DE |
| | | KR |
| AROMATIC | | HFWY |

Preferred polypeptides comprise the RGD motif at amino acids 244 to 246 of SEQ ID NO: 1, such as a fragment comprising amino acids 242 to 252 of SEQ ID NO: 1.

LAP-β1 or a functional variant thereof may be fused to a carrier polypeptide. Thus, additional amino acid residues may be provided at, for example, one or both termini of LAP-β1 or a functional variant thereof for the purpose of providing a carrier polypeptide, by which the polypeptide can be, for example, affixed to a label, solid matrix or carrier. Thus the first component for use in a method of the invention may be in the form of a fusion polypeptide which comprises heterologous sequences. Indeed, in practice it may often be convenient to use fusion polypeptides. This is because fusion polypeptides may be easily and cheaply produced in recombinant cell lines, for example recombinant bacterial or insect cell lines. In addition, fusion polypeptides may be easy to identify and isolate. Typically, fusion polypeptides will comprise a polypeptide sequence as described above and a carrier or linker sequence. The carrier or linker sequence will typically be derived from a non-human, preferably a non-mammalian source, for example a bacterial source. This is to minimize the occurrence of non-specific interactions between sequences in the fusion polypeptide and $\alpha_v\beta_3$.

Polypeptides may be modified by, for example, addition of histidine residues, a T7 tag or glutathione S-transferase, to assist in their isolation. Alternatively, the carrier polypeptide may, for example, promote secretion of the polypeptide from a cell or target expression of the polypeptide to the cell membrane. Amino acids carriers can be from 1 to 400 amino acids in length or more typically from 5 to 200 residues in length. The polypeptide may be linked to a carrier polypeptide directly or via an intervening linker sequence. Typical amino acid residues used for linking are tyrosine, cysteine, lysine, glutamic acid or aspartic acid.

A polypeptide comprising LAP-β1 or a functional variant thereof may be provided in association with the processed TGF-β1 propeptide or a functional variant thereof. That is to say, a small latent complex (SLC) can be used in the invention. Functional variants of the processed TGF-β1 propeptide retain LAP-β1 binding activity and may be obtained according to the description provided above for LAP-β1.

A polypeptide comprising LAP-β1 or a functional variant thereof may be provided in association with the processed TGF-β1 propeptide or a functional variant thereof, and the latent TGF-β1-binding protein (LTBP) or a functional variant thereof. That is to say, a large latent complex (LLC), can be used in the invention. Functional variants of the LTBP retain LAP-β1 binding activity and may be obtained according to the description provided above for LAP-β1.

Suitable polypeptides for use as a first component may be chemically modified, for example, post translationally modified. For example they may be glycosylated or comprise modified amino acid residues. Polypeptides can be in a variety of forms of polypeptide derivatives, including amides and conjugates with polypeptides i.e. LAP-β1 and/or processed TGF-β1 and/or LTBP or functional variants thereof may be so-modified.

Chemically modified polypeptides also include those having one or more residues chemically derivatized by reaction of a functional side group. Such derivatized side groups of a functional side group. Such derivatized side groups include those which have been derivatized to form amine hydrochlorides, p-toluene sulfonyl groups, carbobenzoxy groups, t-butyloxycarbonyl groups, chloroacetyl groups and formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine.

Also included as chemically modified polypeptides are those polypeptides which contain one or more naturally occurring amino acids derivatives of the twenty standard amino acids. For example, 4-hydroxyproline may be substituted for proline or homoserine may be substituted for serine.

LAP-β1 or a functional variant thereof and/or other polypeptides used as part of a first component may carry a revealing label. Suitable labels include radioisotopes such as $^{32}$P or $^{35}$S, fluorescent labels, enzyme labels, or other protein labels such as biotin.

LAP-β1 or a functional variant thereof and/or other polypeptides used as part of a first component may be expressed using recombinant DNA techniques. For example, suitable polypeptides may be expressed in, for example, bacterial or insect cell lines (see, for example, Munger et al., 1998, Molecular Biology of the Cell, 9, 2627–2638). Also, suitable polypeptides may be isolated biochemically from any suitable tissue.

Alternatively, polypeptides may be chemically synthesized. Synthetic techniques, such as a solid-phase Merrifield-type synthesis, may be preferred for reasons of purity, antigenic specificity, freedom from unwanted side products and ease of production. Suitable techniques for solid-phase peptide synthesis are well known to those skilled in the art (see for example, Merrifield et al., 1969, Adv. Enzymol 32, 221–96 and Fields et al., 1990, Int. J. Peptide Protein Res, 35, 161–214). In general, solid-phase synthesis methods comprise the sequential addition of one or more amino acid residues or suitably protected amino acid residues to a growing peptide chain.

Polypeptides for use as a first component in a method of the invention may be linear or cyclic. A linear polypeptide may be cyclised according to any suitable method (see for example Zimmer et al., 1992, Peptides, pp.393–394, ESCOM Science Publishers, BV., 1993 and Gurrath et al., 1992, Eur. J. Biochem., 210, 911–921). Typically, tertbutoxycarbonyl protected polypeptide methyl ester is dissolved in methanol and sodium hydroxide are added and the admixture is reacted at 20° C. to hydrolytically remove the methyl ester protecting group. After evaporating the solvent, the tertbutoxycarbonyl protecting group is extracted with ethyl acetate from acidified aqueous solvent. The tertbutoxycarbonyl protecting group is then removed under mildly acidic conditions in dioxane cosolvent. The unprotected linear peptide with free amino acid and carboxy termini so obtained is converted to its corresponding cyclic polypeptide by reacting a dilute solution of the linear polypeptide in a mixture of dimethylformamide with dicyclohexylcarboiimide in the presence of 1-hydroxy benzotriazole and N-methylmorpholine. The resultant cyclic polypeptide is purified by chromatography.

The second component comprises integrin $\alpha_v\beta_3$ or a functional variant thereof. A functional variant of $\alpha_v\beta_3$ is a polypeptide which shows $\alpha_v\beta_3$-like activity in respect of the ability of $\alpha_v\beta_3$ to bind TGF-$\beta$1. More specifically, the functional variant is able to bind LAP-$\beta$1 of TGF-$\beta$1. Thus, the second component may comprise, for example, a fragment of integrin $\alpha_v\beta_3$ which binds LAP-$\beta$1, or a polypeptide which comprises wild type $\alpha_v\beta_3$ sequences which correspond to LAP-$\beta$1 binding sites and elsewhere comprises non-wild type sequences.

Also, suitable functional variants may comprise non-wild type LAP-$\beta$1 binding sites, but will still be capable of binding LAP-$\beta$1. It may be preferable to use non-wild type binding sites which show an increased binding affinity for LAP-$\beta$1 as compared with the binding affinity of wild type binding sites. Use of such non-wild type binding sites may allow the identification of products which are strong disrupters of LAP-$\beta$1/$\alpha_v\beta_3$ interactions. Non-wild type LAP-$\beta$1 binding sequences will typically arise through substitution, deletion or addition for example, as described for the first component above.

Second component polypeptides may be produced according to similar methods as described for first component polypeptides.

A two component assay can be carried out according to any suitable protocol. Preferably, the assay is adapted so that it can be carried out in a single reaction vessel and more preferably can be carried out in a single well of a plastics microtitre plate and thus can be adapted for high through-put screening. Typically, a cell adhesion assay is carried out.

In a cell adhesion assay, the first component polypeptide is coated on the walls of a suitable vessel, in particular the well of a plastics microtitre plate. In one suitable assay format, the second component, produced, for example, chemically or recombinantly is simply added to the assay vessel. Binding of the second component to the first component can be followed by the use of a second component which carries a label, for example a radioactive label or a fluorescent label.

Alternatively, in another suitable assay format, cells expressing the second component are added to the vessel and allowed to interact with the first component in the presence of a test product. Suitable cells are any cells that express $\alpha_v\beta_3$. Examples of suitable cells are give in, for example Blystone et al (1995) Journal of Cell Biology 130, 745–754.

The number of cells which bind to the first component polypeptide is then determined. This may be carried out by, for example, staining the cells and then carrying out spectrophotometry. Optionally, the stain may be eluted and spectrophotometry carried out on the eluted sample.

It may be necessary to add further components to the reaction mixture in order to promote integrin $\alpha_v\beta_3$ to a suitable activation state for binding to LAP-$\beta$1. In addition, suitable control experiments may be carried out. The cell adhesion assay may be run without the test product present. In order to distinguish between non-specific interactions between the first component and cells expressing the second component, antibodies specific to one of the two polypeptides of integrin $\alpha_v\beta_3$ may be added to the reaction mixture. Control cells expressing polypeptides other than $\alpha_v\beta_3$ may be used, to distinguish between specific reactions between the first and second components and non-specific reactions between $\alpha_v\beta_3$ and other surface proteins of the cells expressing the second component.

The invention also provides a test kit for the identification of a modulator of the interaction of LAP-$\beta$1 and $\alpha_v\beta_3$. A kit according to the invention comprises a first component as described above and a second component as described above. In a preferred kit of the invention, the kit also comprises a means for determining whether a test product modulates the interaction between the first and second components. Typically, a test kit will provide suitable components for carrying out an adhesion assay as described above. Thus, the second component may be provided in the form of cells which express the second component. If the kit is an adhesion assay kit, the kit may also comprise a suitable stain for quantifying the amount of cells which bind to the first component, for example crystal violet stain.

A kit of the invention may optionally further comprise, appropriate buffer(s), control cells, expressing for example integrins other than $\alpha_v\beta_3$ or control antibodies. A kit of the invention may also comprise appropriate packaging and instructions for use in a method for the identification of a modulator of the interaction between LAP-$\beta$1 and $\alpha_v\beta_3$.

Suitable test products for use in methods of the invention include combinatorial libraries, defined chemical entities, peptides and peptide mimetics, oligonucleotides and natural product libraries. Test products may be used in an initial screen of, for example, ten substances per reaction, and the products of batches which show inhibition tested individually. Furthermore, antibody products (for example, monoclonal and polyclonal antibodies, single chain antibodies, chimaeric antibodies, CDR-grafted antibodies and humanized antibodies) may be used.

A modulator of the interaction between LAP-$\beta$1 and $\alpha_v\beta_3$ is one which produces a measurable reduction or increase in the degree of interaction between those two proteins in a method of the invention. Thus, modulators of the interaction between LAP-$\beta$1 and $\alpha_v\beta_3$ may be inhibitors or activators of that interaction.

An inhibitor of the interaction between LAP-$\beta$1 and $\alpha_v\beta_3$ is one which causes the degree of interaction between those proteins to be reduced or substantially eliminated, as compared to the degree of interaction between the two, in the absence of that inhibitor. Preferred inhibitors are those which inhibit the LAP-$\beta$1/$\alpha_v\beta_3$ interaction by at least 10%, at least 20%, at least 30%, at least 40%, at least 50%, at least 60%, at least 70%, at least 80%, at least 90%, at least 95% or at least 99% at a concentration of the inhibitor of 1 $\mu$gml$^{-1}$, 10 $\mu$gml$^{-1}$, 100 $\mu$gml$^{-1}$, 500 $\mu$gml$^{-1}$, 1 mgml$^{-1}$, 10 mgml$^{-1}$, 100 mg ml$^{-1}$. The percentage inhibition represents the percentage decrease in the interaction between LAP-$\beta$1/$\alpha_v\beta_3$ in a comparison of assays in the presence and absence of the test substance. Any combination of the above mentioned degrees of percentage inhibition and concentration of inhibitor may be used to define an inhibitor of the invention, with greater inhibition at lower concentrations being preferred.

An activator of the interaction between LAP-$\beta$1 and $\alpha_v\beta_3$ is one which causes the degree of interaction between those proteins to be increased, as compared to the degree of interaction between the two in the absence of that activator. Preferred activators are those which activate the LAP-$\beta$1/$\alpha_v\beta_3$ interaction by at least 10%, at least 25%, at least 50%, at least 100%, at least 200%, at least 500% or at least 1000% at a concentration of the activator of 1 $\mu$g ml$^{-1}$, 10 $\mu$g ml$^{-1}$, 100 $\mu$g ml$^{-1}$, 500 $\mu$g ml$^{-1}$, 1 mg ml$^{-1}$, 10 mg ml$^{-1}$, 100 mg ml$^{-1}$. The percentage activation represents the percentage increase in the interaction between LAP-$\beta 1/\alpha_v\beta_3$ in a comparison of assays in the presence and absence of the test substance. Any combination of the above mentioned degrees of percentage activation and concentration of activator may be used to define an activator of the invention, with greater activation at lower concentrations being preferred.

Test products which show activity in assays such as those described above can be tested in in vivo systems, such as an animal disease model. Thus, candidate inhibitors could be tested for their ability to attenuate inflammation and/or fibrosis in mice. A candidate activator could be tested for its ability to prevent apoptosis in mice.

It is preferable that inhibitors or activators of the interaction between LAP-$\beta 1$ and $\alpha_v\beta_3$ do not disrupt the interaction between LAP-$\beta 1$ and other integrins such as $\alpha_v\beta_1$, $\alpha\beta_5$ or $\alpha_v\beta_6$. That is, inhibitors or activators are generally specific for the interaction between LAP-$\beta 1$ and $\alpha_v\beta_3$.

Suitable inhibitors may include functional variants of $\alpha_v\beta_3$, fragments thereof, mimetics of either $\alpha_v\beta_3$ or a natural ligand of $\alpha_v\beta_3$, for example polypeptides based on TGF-$\beta 1$ that mimic the structural region involved in $\alpha_v\beta_3$/LAP-$\beta 1$ binding interactions, polypeptides having a sequence corresponding to a functional binding domain of LAP-$\beta 1$ for $\alpha_v\beta_3$ and antibodies which immunoreact with either LAP-$\beta 1$ or $\alpha_v\beta_3$.

Suitable activators include functional variants of LAP-$\beta 1$ or LAP-$\beta 3$.

Modulators of the invention may be in substantially purified form. They may be in substantially isolated form, in which case they will generally comprise at least 80% e.g. at least 90, 95, 97 or 99% by weight of the dry mass in the preparation. The product is typically substantially free of other cellular components. The product may be used in such a substantially isolated, purified or free form in the method or be present in such forms in a kit.

Modulators of the invention may be used in a method of treatment of the human or animal body by therapy.

In particular, inhibitors of the invention may be use in a method of immunomodulation or in a method of treatment of an inflammatory disease, a fibrotic disease, cancer (including solid tumor therapy and metastatic tumor therapy), diabetic retinopathy, bone resorption or osteoporosis. Examples of conditions which involve an inflammatory and/or fibrotic component are chronic obstructive pulmonary disorder, rheumatoid arthritis, psoriasis, restenosis, atherosclerosis, liver fibrosis and asthma. The condition of a patient requiring an inhibitor of the interaction between LAP-$\beta 1$ and $\alpha_v\beta_3$ can be improved by administration of an inhibitor of the invention. A therapeutically effective amount of an inhibitor of the invention may be given to a host in need thereof.

Activators of the invention may be used in a method of preventing (i.e. protection against) apoptosis. The condition of a patient requiring an activator of the interaction between LAP-$\beta 1$ and $\alpha_v\beta_3$ can be improved by administration of an activator of the invention. A therapeutically effective amount of an activator of the invention may be given to a host in need thereof.

Modulators of the interaction between LAP-$\beta 1$ and $\alpha_v\beta_3$ may be administered in a variety of dosage forms. Thus, they can be administered orally, for example as tablets, troches, lozenges, aqueous or oily suspensions, dispersible powders or granules. The modulators may also be administered parenterally, either subcutaneously, intravenously, intramuscularly, intrasternally, transdermally or by infusion techniques. The modulators may also be administered as suppositories. A physician will be able to determine the required route of administration for each particular patient.

The formulation of a modulator for use in preventing or treating one of the above-mentioned conditions will depend upon factors such as the nature of the exact modulator, whether a pharmaceutical or veterinary use is intended, etc. A modulator may be formulated for simultaneous, separate or sequential use.

A modulator is typically formulated for administration in the present invention with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

A therapeutically effective amount of a modulator is administered to a patient. The dose of a modulator may be determined according to various parameters, especially according to the substance used; the age, weight and condition of the patient to be treated; the route of administration; and the required regimen. Again, a physician will be able to determine the required route of administration and dosage for any particular patient. A typical daily dose is from about 0.1 to 50 mg per kg of body weight, according to the activity of the specific modulator, the age, weight and conditions of the subject to be treated, the type and severity of the degeneration and the frequency and route of administration. Preferably, daily dosage levels are from 5 mg to 2 g.

The following Examples illustrate the invention:

EXAMPLES

Materials & Methods

Unless indicated otherwise, the techniques and methodologies described are standard biochemical techniques. Examples of suitable general methodology textbooks include Sambrook et al., Molecular Cloning (1995), John Wiley & Sons, Inc.

Cell Culture

K562-WT (wild-type), K562-$\alpha_v\beta_6$, K562-$\alpha_v\beta_5$, K562-$\alpha_v\beta_3$, and HL60 cells were maintained in 1:1 RPMI 1640, Hepes modification (Gibco): Dulbecco's Minimum Essential Medium (DMEM), Hepes modification (Sigma) supplemented with L-glutamine (Gibco) and 10% fetal calf serum (FCS). In addition K562-$\alpha_v\beta_3$, K562-$\alpha_v\beta_5$, and K562-$\alpha_v\beta_6$ cells were supplemented with geneticin (G418, Gibco) at 1 mg/ml. All transfected cells were generated by transfecting K562 cells with pCDNA-3 constructs containing individual integrin cDNAs, using lipofectamine plus (Gibco BRL). Stable G418-resistant populations were shown to express the required integrin and possess the expected adhesion properties of that integrin.

Antibodies and Other Reagents

Antibody clones used were as follows. The anti-$\beta_1$ integrin antibody clone 4B4 was obtained from Coulter. The anti-$\alpha_5$ antibody clone SAM-1, and anti-$\alpha_v$ integrin antibody clone 69-6-5, were obtained from Immunotech. The anti-$\alpha_v\beta_3$ integrin antibody clone LM609, anti-$\alpha_v\beta_6$ integrin antibody clone 10D5, and anti-$\alpha_v\beta_5$ integrin antibody clone P1F6, were from Chemicon. The isotype control (MOPC21) was from Sigma. The $\alpha_v\beta_3/\alpha_v\beta_5$ inhibitor GW372205X (also called SB223245) was synthesized in house. GW372205X/SB223245 is described in WO-A-96/00730 (SmithKline Beecham Corp) and Keenan et al (1997) J. Med. Chem. 40, 2289–2292. LAP-$\beta$1 was obtained from Sigma, fibrinogen was obtained from Calbiochem, and vitronectin was purified from human plasma.

Adhesion Assays

All proteins were coated onto Maxisorp 96-well plates (Nunclon) overnight at 4° C. Each protein was diluted in PBS at the concentrations indicated, and a total volume of 100 ul added per well. Plates were washed twice in PBS then blocked with 3% BSA/PBS for 1 hour at 37° C., and finally washed twice in PBS. Cells were pelleted and washed once in HBSS (Sigma) then spread in HBSS, 25 mM HEPES pH 7.5 at the desired cell concentration (K562-WT, K562-$\alpha_v\beta_6$, HL60 at 6×10$^6$ cells/ml, K562-$\alpha_v\beta_5$, K562-$\alpha_v\beta_3$ at 4×10$^6$ cells/ml, 100 ul per well), in the presence of either 2 mM MgCl$_2$ or 0.5 mM MnCl$_2$ as indicated in the figure legends. Other additions are detailed in the figure legends. For antibody inhibition cells were pre-incubated with the antibody (10 µg/ml) on ice for 5 minutes. Cells were then allowed to attach for 35 minutes at 37° C., washed twice with PBS, once in ethanol, and fixed in ethanol for 20 minutes at room temperature. For quantitation cells were visualised by staining with 0.1% crystal violet (Sigma) for 10 minutes then lysed in 0.5% Triton X-100 (Sigma) and read optically at 570 nm in a Wallac Victor plate reader.

Example 1

Adhesion of Various Integrins to LAP-$\beta$1

Figure 1:
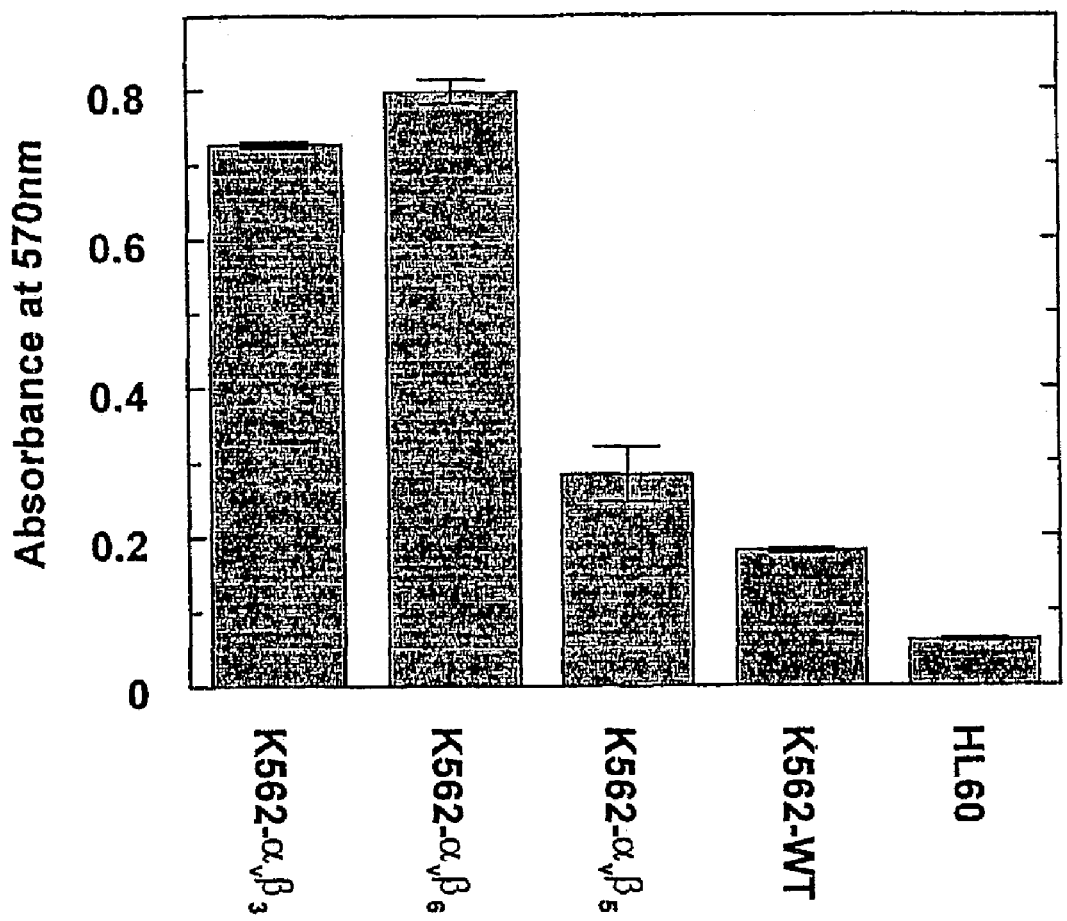
FIG. 1 shows the adhesion of various cells to LAP-β1. Cells were allowed to attach to wells coated with LAP-β1 at 10 μg/ml. Cells were incubated for 35 minutes at 37° C. in HBSS supplemented with 25 mM HEPES pH 7.5, and either 0.5 mM MnCl$_2$ (K562-WT, HL60, K562-$\alpha_v\beta_6$) or 2 mM MgCl$_2$ (K562-$\alpha_v\beta_3$, K562-$\alpha_v\beta_5$). Each bar represents the mean±SD of duplicated points.

To determine which integrins interact with LAP-$\beta$1, a variety of cell types were allowed to adhere to LAP-$\beta$1 (FIG. 1). In agreement with the literature (Munger et al., 1999, Cell 96, 319–328) K562-$\alpha_v\beta_6$ cells adhered to LAP$\beta_1$. K562-WT cells bound slightly to LAP-$\beta$1, as did K562-$\alpha_v\beta_5$ cells. The K562-$\alpha_v\beta_5$ cell binding also agrees with the literature (Munger et al., 1998, supra) which shows that $\alpha_v\beta_5$ is a weak ligand for LAP-$\beta$1, and this weak binding was inhibited by the $\alpha_v\beta_5$-blocking antibody P1F6 (data not shown). The K562-WT binding suggests that $\alpha_5\beta_1$ may also be a weak ligand for LAP-$\beta$1 as this binding was inhibited by the $\alpha_5\beta_1$ blocking antibody SAM-1. HL60 Cells failed to bind LAP-$\beta$1 indicating that, at least in this cell type, $\alpha_4\beta_1$, $\alpha_5\beta_1$, and $\alpha_L\beta_2$ are not receptors for LAP-$\beta$1 under there adhesion conditions. K562-$\alpha_v\beta_3$ interacted strongly with LAP-$\beta$1, binding comparably to the K562-$\alpha_v\beta_6$ cells. This suggested that $\alpha_v\beta_3$ was a receptor for LAP-$\beta$1 binding.

Example 2

Specificity of K562-$\alpha_v\beta_3$ Cell Binding to LAP-$\beta$1

Figure 2:
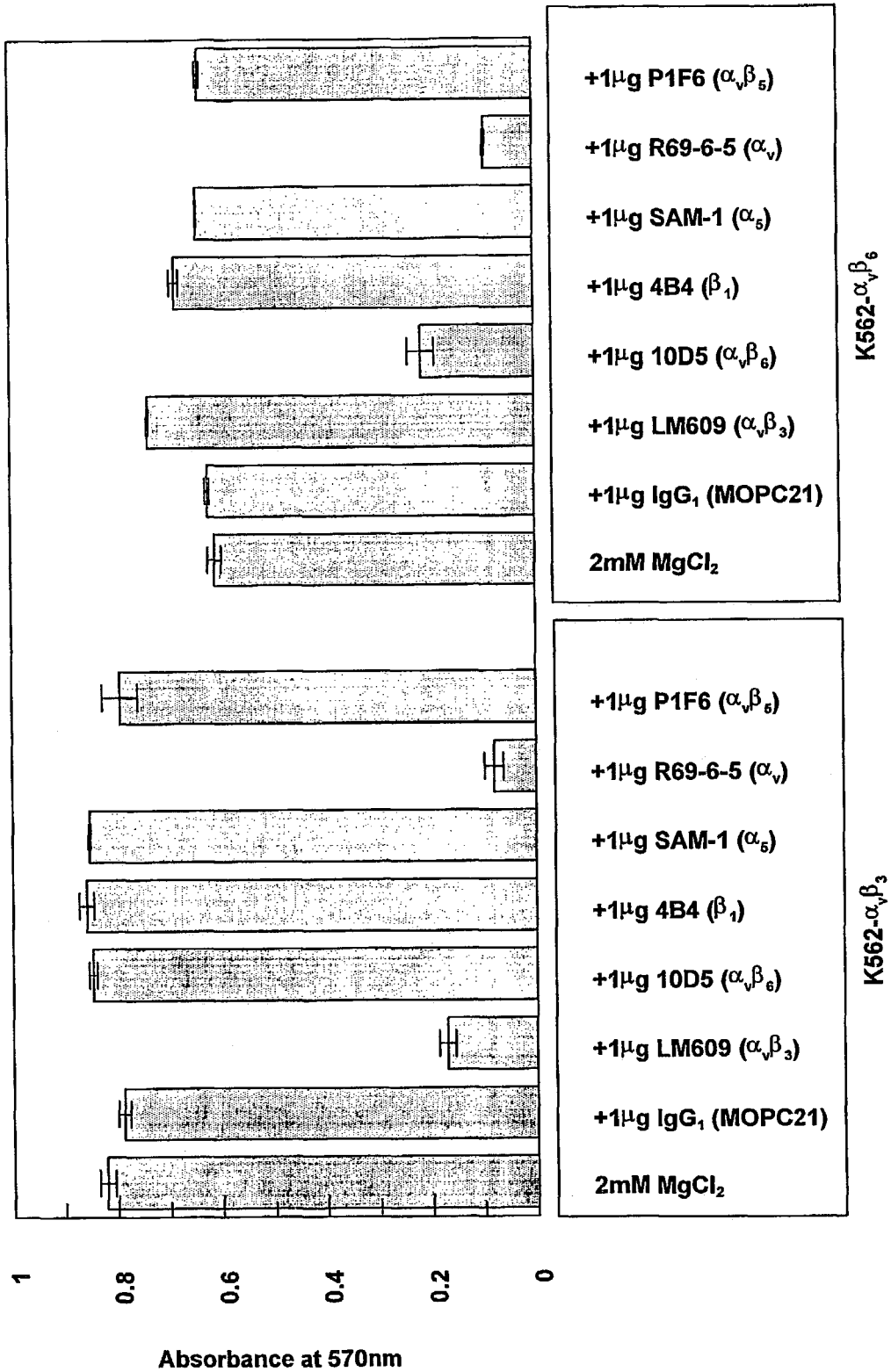
FIG. 2 shows that K562-$\alpha_v\beta_3$ and K562-$\alpha_v\beta_6$ Cells Adhere to LAP-β1 via the $\alpha_v\beta_3$ and $\alpha_v\beta_6$ integrins respectively. Cells were allowed to attach to wells coated with LAP-β1 at 10 μg/ml. Cells were incubated for 5 minutes on ice, then for 35 minutes at 37° C., in the presence of antibodies at 10 μg/ml as indicated. The buffer used was HBSS supplemented with 25 mM HEPES pH 7.5, and 2 mM MgCl$_2$. Each bar represents the mean±SD of duplicated samples.

To define the K562-$\alpha_v\beta_3$ cell interaction with LAP-$\beta$1, specific integrin blocking antibodies were tested for the ability to inhibit adhesion to (FIG. 2). Adhesion of K562-$\alpha_v\beta_3$ cells to LAP-$\beta$1 was inhibited by the $\alpha_v\beta_3$ blocking antibody clone LM609, and the $\alpha_v$ blocking clone 69-6-5. In contrast, an IgG isotype control (MOPC21) and blocking antibodies against $\alpha_v\beta_6$ (10D5), $\beta_1$ (4B4), $\alpha_5\beta_1$ (SAM-1), or $\alpha_v\beta_5$ (P1F6) were inactive. For K562-$\alpha_v\beta_6$ cell binding to LAP-$\beta$1, both the $\alpha_v$ blocking antibody clone 69-6-5 and the $\alpha_v\beta_6$ blocking antibody clone 10D5 displayed inhibitory activity, whilst antibodies to $\alpha_v\beta_3$ (LM609), $\beta_1$ (4B4), $\alpha_5\beta_1$ (SAM-1), $\alpha_v\beta_5$ (P1F6), and an isotype control (MOPC21) were all inactive. These data clearly show that K562-$\alpha_v\beta_3$ cells bind to LAP-$\beta$1 via the $\alpha_v\beta_3$ integrin, whilst K562-$\alpha_v\beta_3$ cells bind via the $\alpha_v\beta_6$ integrin.

Example 3

Adhesion Properties of K562-$\alpha_v\beta_3$ Cells to LAP-$\beta$1

Figure 3:
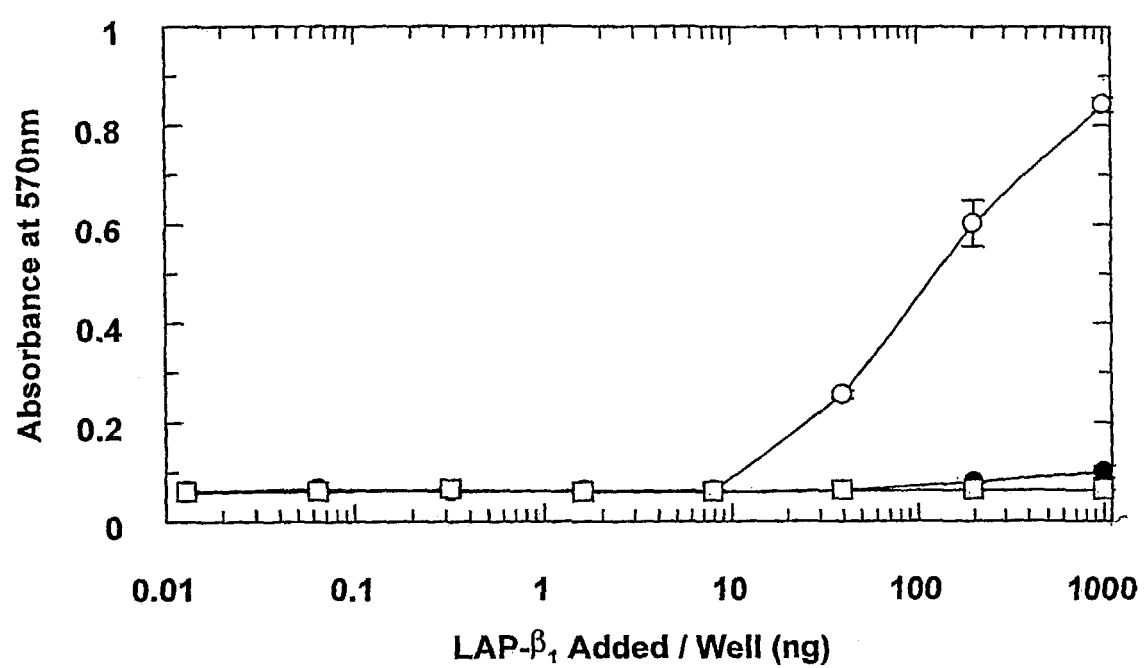
FIG. 3 shows that K562-$\alpha_v\beta_3$ cells bind to LAP-β1 in a concentration-dependent manner via $\alpha_v\beta_3$. Cells were allowed to attach to wells coated with quantities of LAP-β1 indicated. Cells were incubated for 5 minutes on ice, then for 35 minutes at 37° C., in the presence of either nothing (open circles), 10 μg/ml LM609 (filled circles), or 5 μM GW372205X (Open squares). The buffer used was HBSS supplemented with 25 mM HEPES pH 7.5, and 2 mM MgCl$_2$. Each data point represents the mean±SD of duplicated samples.

To further examine the characteristics of K562-$\alpha_v\beta_3$ cell binding to LAP-$\beta$1, a titration experiment was performed to determine the concentrations of LAP-$\beta$1 required to support binding of $\alpha_v\beta_3$ FIG. 3). K562-$\alpha_v\beta_3$ cells bound to LAP-$\beta$1 in the concentration range 40 ng/well to 1 µg/well. However, binding does not appear to be maximal by 1 µg/well LAP-$\beta$1. Binding at all levels of LAP-$\beta$1 is completely inhibited by the $\alpha_v\beta_3$ blocking antibody (LM$^{609}$) and by the $\alpha_v\beta_3/\alpha_v\beta_5$ small molecule inhibitor GW372205X (SB223245) at 10 µM. This demonstrates that K562-$\alpha_v\beta_3$ cells bind to LAP-$\beta$1 as expected over a wide concentration range via the $\alpha_v\beta_3$ integrin.

Example 4

Figure 4:
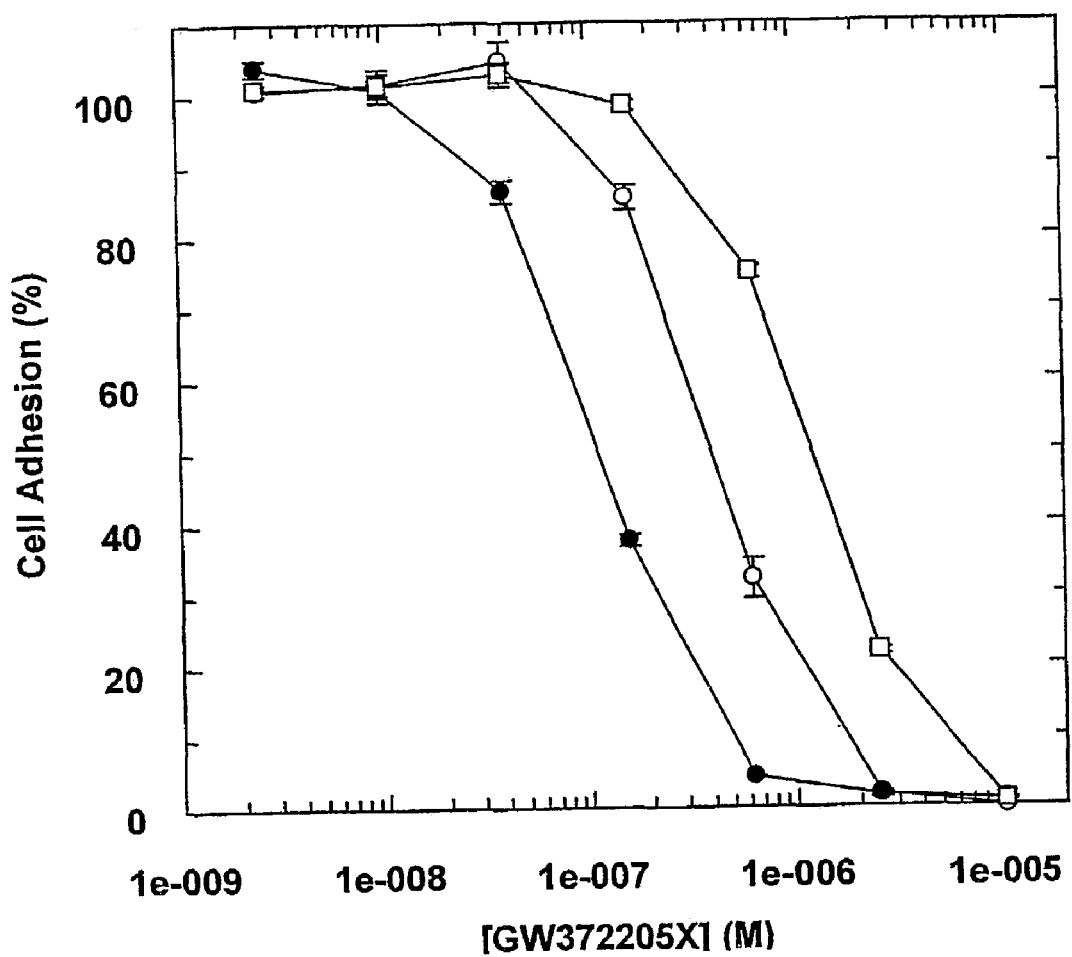
FIG. 4 shows inhibition of K562-$\alpha_v\beta_3$ cell binding to Fibrinogen, Vitronectin, and LAPβ$_1$ by GW372205X. Cells were allowed to attach to wells coated with either 10 μg/ml LAP-β1 (Open circles), 10 μg/ml Vitronectin (open squares), or 1 mg/ml Fibrinogen (closed circles) for 35 minutes at 37° C., in the presence of various concentration of GW372205X from 2.5 nM up to 10 μM. The buffer used was HBSS supplemented with 25 mM HEPES pH 7.5, and 2 mM MgCl$_2$. Adhesion to each ligand in the absence of compound was taken as a 100% binding value, with adhesion to BSA alone as a 0% binding value. The 100% binding values corresponded to the following absorbances at 570 nm: Fibrinogen=0.8, Vitronectin=0.9, LAP-β1=0.9. Each data point represents the mean±SD of duplicated samples.

Comparison of GW372205X Potency on K562-$\alpha_v\beta_3$ Binding to a Variety of Ligands To compare LAP-$\beta$1 as an $\alpha_v\beta_3$ ligand relative to other known ligands, the inhibitory potency of GW372205X was tested on K562-$\alpha_v\beta_3$ cell binding to LAP-$\beta$1, Fibrinogen, and Vitronectin. FIG. 4 shows that GW372205X was most effective at blocking the $\alpha_v\beta_3$: fibrinogen interaction, and less effective at blocking the $\alpha_v\beta_3$: vitronectin interaction. The inhibitory activity of GW372205X towards the $\alpha_v\beta_3$: LAP-$\beta$1 interaction lies within this range. This data shows that LAP-$\beta$1 behaves similarly to fibrinogen and vitronectin in terms of small molecule inhibition of $\alpha_v\beta_3$.

Example 5

Figure 5:
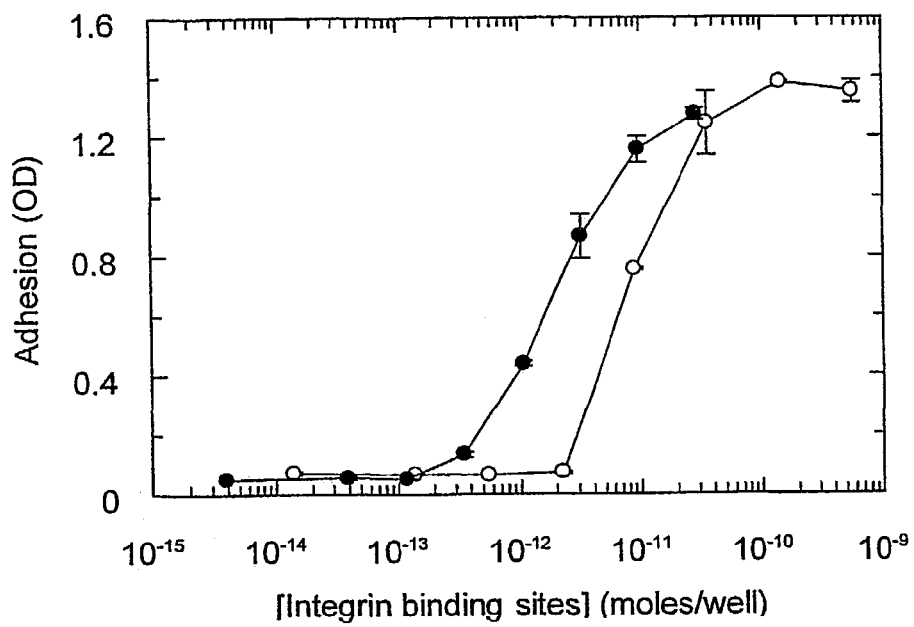
FIG. 5. Adhesion of K562-$\alpha_v\beta_3$ Cells to Intact LAPβ$_1$ and GST-LAPβ$_1$ (amino acids 242–252).

Adhesion of K562-$\alpha_v\beta_3$ Cells to GST-LAP$\beta_1$ Minimal Binding Domain $\alpha_v\beta_3$ can interact with ligands via both RGD and non-RGD motifs. To conclusively demonstrate that the RGD motif in LAPβ$_1$ is the α$_v$β$_3$ binding site requires mutation of each of these three residues to alanine to correlate with a subsequent loss of α$_v$β$_3$ adhesion. To facilitate this we chose to express a peptide fragment of LAPβ$_1$ (amino acids 242–252 where the amino acid sequence is $^{242}$GRRGD-LATIHG$^{252}$) containing the RGD motif as a GST fusion protein in *E. coli*. This GST-LAPβ$_1$ (aa242–252) protein was compared to intact LAPβ$_1$ in a matrix titration experiment to determine the amounts of ligand required to support adhesion of K562-α$_v$β$_3$ cells (FIG. 5). Such analysis showed that the GST-LAPβ$_1$ (aa242–252) protein supported adhesion of K562-α$_v$β$_3$ cells similarly to intact LAPβ$_1$. In addition, SB223245 inhibited K562-α$_v$β$_3$ cell adhesion to intact LAPβ$_1$ and GST-LAPβ$_1$ (aa242–252) with similar IC$_{50}$ values of 442 nM and 139 nM respectively (FIG. 6). These data show that the GST-LAPβ$_1$ (aa242–252) protein effectively mimics the intact LAPβ$_1$ protein for binding to α$_v$β$_3$, suggesting that the α$_v$β$_3$ binding motif lies within amino acids 242–252.

Example 6

K562-α$_v$β$_3$ Cells Adhere to LAPβ$_1$ via the RGD Motif

Having identified a minimal α$_v$β$_3$ recognition sequence of LAPβ$_1$, fusion proteins were used to analyse the importance of the RGD motif in GST-LAPβ$_1$ (amino acid 242–252). Either Arg$_{245}$, Gly$_{246}$, or Asp$_{247}$ were separately exchanged for alanine, and the mutant proteins tested for their ability to support adhesion of K562-α$_v$β$_3$ cells (FIG. 7). Mutation of any of the three RGD residues abolished binding, clearly demonstrating that α$_v$β$_3$ interacts directly with LAPβ$_1$ at the RGD motif.

The invention claimed is:

1. A method for the identification of an inhibitor of the interaction between latency associated peptide of transforming growth factor-β1 (LAP-β1) and the integrin $\alpha_v\beta_3$, which method comprises:
   (a) providing, as a first component, LAP-β1 consisting of amino acids 30–278 of SEQ ID NO:1 in the form of a monomer or a homodimer;
   (b) providing, as a second component, integtin $\alpha_v\beta_3$;
   (c) contacting the two components with a test product under conditions that, in the absence of the test product, would permit the two components to interact, where the conditions include the presence of cations; and
   (d) determining whether the test product is capable of inhibiting the interaction between the first and second components, thereby determining whether the test product is an inhibitor of the interaction between (LAP-β1) and integrin $\alpha_v\beta_3$.

2. A method according to claim 1, wherein in step (a) LAP-β1 is provided in the form of a monomer.

3. A method according to claim 1, wherein in step (a) LAP-β1 is provided in the form of a homoclimer of two peptides, each peptide consisting of amino acids 30–278 of SEQ ID NO:1.

4. A method according to claim 3, wherein said homodimer is a component of a small latency complex (SLC).

5. A method according to claim 3, wherein said homodimer is a component of a large latency complex (LLC).

6. A method for the identification of an inhibitor of the interaction between latency associated peptide of transforming growth factor-β1 (LAP-β1) and the integrin $\alpha_v\beta_3$, which method comprises:
   (a) providing as a first component, a peptide consisting of a sequence with at least 98% sequence identity to amino acids 30–278 of SEQ ID NO:1 and containing amino acids 242–252 of SEQ ID NO:1, and having integrin $\alpha_v\beta_3$ binding activity;
   (b) providing, as a second component, integrin $\alpha_v\beta_3$;
   (c) contacting the two components with a test product under conditions that, in the absence of the test product would permit the two components to interact, where the conditions include the presence of cations; and
   (d) determining whether the test product is capable of inhibiting the interaction between the first and second components, thereby determining whether the test product is an inhibitor of the interaction between LAP-β1 and integrin $\alpha_v\beta_3$.

* * * * *